US008058673B2

(12) United States Patent
Kim et al.

(10) Patent No.: US 8,058,673 B2
(45) Date of Patent: Nov. 15, 2011

(54) BIOSENSOR USING NANODOT AND METHOD OF MANUFACTURING THE SAME

(75) Inventors: Tae Youb Kim, Seoul (KR); Chil Seong Ah, Daejeon (KR); Chang Geun Ahn, Daejeon (KR); Han Young Yu, Daejeon (KR); Jong Heon Yang, Daejeon (KR); Moon Gyu Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 413 days.

(21) Appl. No.: 12/240,133

(22) Filed: Sep. 29, 2008

(65) Prior Publication Data
US 2010/0283031 A1 Nov. 11, 2010

(30) Foreign Application Priority Data
Dec. 10, 2007 (KR) .................. 10-2007-0127565

(51) Int. Cl.
*H01L 29/72* (2006.01)
(52) U.S. Cl. ............ 257/253; 257/9; 324/252; 977/721; 977/784; 977/938
(58) Field of Classification Search .............. 257/9, 253; 324/252; 977/721, 784, 938
See application file for complete search history.

(56) References Cited

U.S. PATENT DOCUMENTS
6,870,235 B2  3/2005 Abstreiter et al.

FOREIGN PATENT DOCUMENTS
JP  2006-258661  9/2006
WO  WO 02/48701 A2  6/2002
WO  WO 2007/114649 A1  10/2007

OTHER PUBLICATIONS

Eric Stern et al., "Label-free immunodetection with CMOS-compatible semiconducting nanowires", Letters, vol. 445, Feb. 2007, doi: 10.1038/Nature 05498, 2007 Nature Publishing Group, pp. 519-522.
Yi Cui et al., "Nanowire Nanosensors for Highly Sensitive and Selective Detection of Biological and Chemical Species", www.sciencemag.org, Science vol. 293, Aug. 17, 2001, pp. 1289-1292.
Fernando Patolsky et al., "Nanowire nanosensors," Materials today, Apr. 2005, pp. 20-28, Elsevier Ltd.

*Primary Examiner* — Edward Wojciechowicz

(57) ABSTRACT

A biosensor using a nanodot and a method of manufacturing the same are provided. A silicon nanowire can be formed by a CMOS process to reduce manufacturing costs. In addition, an electrically charged nanodot is coupled to a target molecule to be detected, in order to readily change conductivity of the silicon nanowire, thereby making it possible to implement a biosensor capable of providing good sensitivity and being manufactured at a low cost.

7 Claims, 6 Drawing Sheets

BIOSENSOR USING NANODOT AND METHOD OF MANUFACTURING THE SAME

CROSS-REFERENCE TO RELATED APPLICATION

This application claims priority to and the benefit of Korean Patent Application No. 2007-127565, filed Dec. 10, 2007, the disclosure of which is incorporated herein by reference in its entirety.

BACKGROUND

1. Field of the Invention

The present invention relates to a biosensor using a nanodot and a method of manufacturing the same, and more particularly, to a biosensor capable of providing good sensitivity at a low cost, and a method of manufacturing the same.

This work was supported by the IT R&D program of MIC/IITA[2006-S-007-02, Ubiquitous Health Monitoring Module and System Development].

2. Discussion of Related Art

In general, a biosensor is a device for measuring variation depending on biochemical, optical, thermal, or electrical reaction. The latest tendency in research has been toward research on an electrochemical biosensor.

The electrochemical biosensor senses variation of conductivity generated from a reaction between a target molecule and a probe molecule in a silicon nanowire to detect a specific biomaterial. A structure and an operation of the electrochemical biosensor will be described in detail with reference to FIG. 1.

FIG. 1 is a view showing the structure and operation of a conventional electrochemical biosensor.

Referring to FIG. 1, the conventional electrochemical biosensor 100 includes a semiconductor substrate 110, a source S and a drain D formed on the semiconductor substrate 110, and a straight silicon nanowire 150 disposed between the source S and the drain D. The silicon nanowire 150 is insulated from the semiconductor substrate 110 by an insulating layer 120, and probe molecules P are fixed to a surface of the silicon nanowire 150. When target molecules T are injected through a fluid pipe (not shown), the target molecules T react with the probe molecules P to vary an electric field of the silicon nanowire 150. Therefore, electric potential of the surface of the silicon nanowire 150 is varied to change conductivity of the silicon nanowire 150. By observing the variation of the conductivity in real time, it is possible to detect the target molecules T.

In the conventional electrochemical biosensor, detection sensitivity is in reverse proportion to the width of the silicon nanowire 150, to which the probe molecules 40 are fixed. In recent times, the silicon nanowire has been formed in a bottom-up type or top-down type, which have the following disadvantages, respectively.

First, in the bottom-up type, carbon nanotubes grown through a chemical vapor deposition (CVD) method or silicon nanowires formed through a vapor-liquid solid (VLS) growth method are aligned to a specific position to manufacture a biosensor.

While the silicon nanowires formed through the bottom-up type have very good electrical characteristics, the silicon nanowires must be aligned using an electrophoresis method or fluid flow through a fluid channel in order to align the silicon nanowires at a desired position, making it difficult to control the position when the silicon nanowires are aligned.

On the other hand, in the top-down type, the silicon nanowires are formed through a patterning and etching process using CMOS process technology.

However, since electrical characteristics of the silicon nanowires formed through the top-down type are worse in comparison with the nanowires formed through the bottom-up type, fine patterning technology (electron beam lithography) with nano accuracy must be used, increasing manufacturing cost.

That is, in order to commercialize the biosensor, it must be possible to provide good sensitivity and be manufactured at a low cost.

SUMMARY OF THE INVENTION

The present invention is directed to a biosensor that has good sensitivity and can be manufactured at a low cost, and a method of manufacturing the same.

One aspect of the present invention provides a biosensor using a nanodot including: a source and a drain formed on a substrate; a silicon nanowire formed between the source and the drain; a probe molecule fixed to the silicon nanowire; and a target molecule coupled to an electrically charged nanodot to react with the probe molecule.

Another aspect of the present invention provides a method of manufacturing a biosensor using a nanodot comprising: forming a source and a drain on a semiconductor substrate; forming a silicon nanowire between the source and the drain; fixing a probe molecule to the silicon nanowire; and coupling an electrically charged nanodot to a target molecule reacting with the probe molecule to inject the nanodot into the silicon nanowire.

Here, the nanodot may be formed of a material which readily couples to the target molecule and is electrically charged, and the silicon nanowire may be formed by a CMOS process. In addition, a line width of the silicon nanowire may be determined depending on the type and size of the nanodot.

BRIEF DESCRIPTION OF THE DRAWINGS

The above and other features of the present invention will be described in reference to certain exemplary embodiments thereof with reference to the attached drawings in which.

DETAILED DESCRIPTION OF PREFERRED EMBODIMENTS

Figure 1:
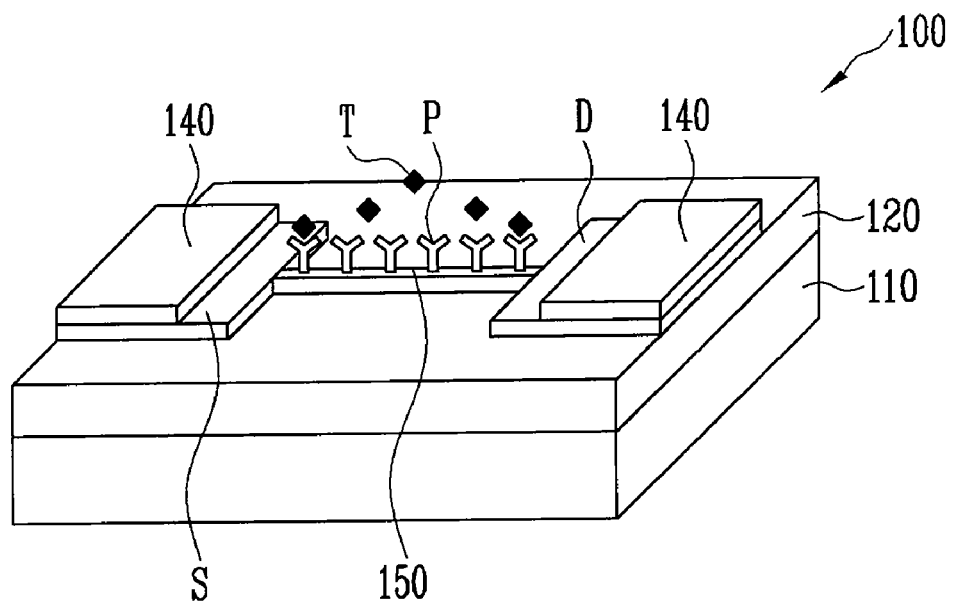
FIG. 1 is a perspective view showing the structure and operation of a conventional electrochemical biosensor.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the following description, when it is mentioned that a layer is disposed "on" another layer or a substrate, it means that the layer may be directly formed on the other layer or a third layer may be interposed therebetween. In the drawings, the thickness of layers and regions are exaggerated for clarity. Like reference numerals designate like elements throughout the specification.

A bio sensor in accordance with the present invention will now be described in detail with reference to the accompanying drawings.

Figure 2:
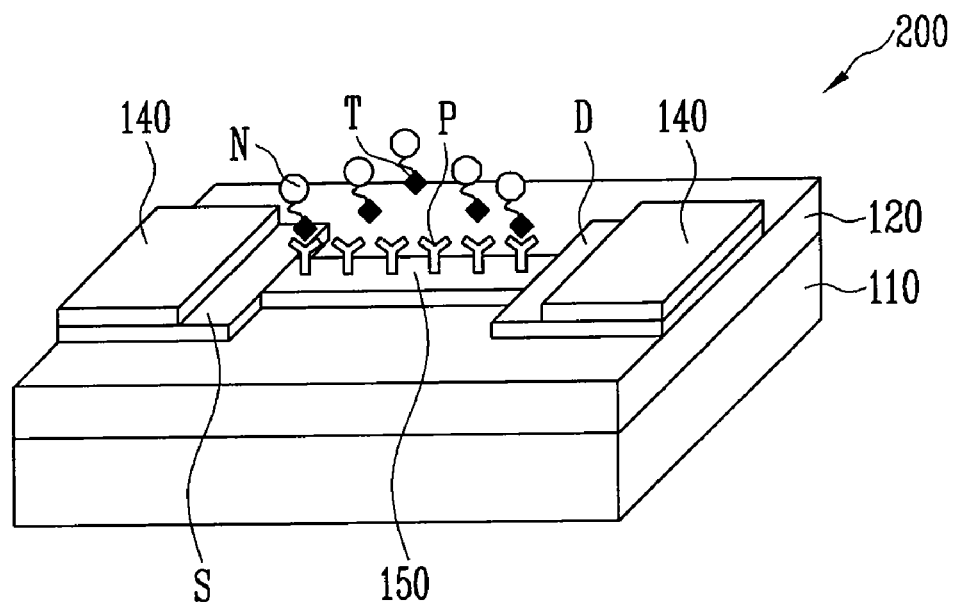
FIG. 2 is a perspective view showing the structure and operation of a biosensor in accordance with an exemplary embodiment of the present invention.

FIG. 2 is a perspective view showing the structure and operation of a biosensor in accordance with an exemplary embodiment of the present invention.

Referring to FIG. 2, a biosensor 200 in accordance with an exemplary embodiment of the present invention is similar to the conventional biosensor 100, except that a silicon nanowire 150 is formed by a CMOS process, and electrically charged nanodots N are coupled to target molecules T to be injected into the silicon nanowire 150.

Here, probe molecules P and target molecules T are formed of any one selected from the group consisting of an antigen, an antibody, DNA, protein, and a combination thereof. For example, when a user wants to detect a prostate specific antigen (PSA) included in blood, first, blood plasma reacting with the prostate specific antigen is fixed to the silicon nanowire 150. Then, when blood is injected from the exterior, the prostate specific antigen included in the blood specifically reacts with the blood plasma fixed to the silicon nanowire 150. Therefore, an electric field is generated around the silicon nanowire 150 to vary conductivity of the silicon nanowire 150.

The electrically charged nanodots N may be formed of a material capable of readily coupling to target molecules T and being electrically charged, for example, silicon, silicon compound, metal compound, and so on, and a width of the silicon nanowire 150 may be varied depending on a constituent and a size of the electrically charged nanodots N. In addition, the size of the electrically charged nanodots N may be about 1 to 50 nm, and a method of electrically charging nanodots may be an electrical method, in addition to an optical method.

In the case that the electrically charged nanodots N are coupled to the target molecules T to be injected into the silicon wire 150 having the probe molecules P, when the target molecules T are coupled to the probe molecules P, an electric field region of the silicon nanowire 150 is enlarged due to the nanodots N coupled to the target molecules T such that conductivity of the silicon nanowire 150 can be readily changed. A description thereof will now be described in detail.

Figure 3A:
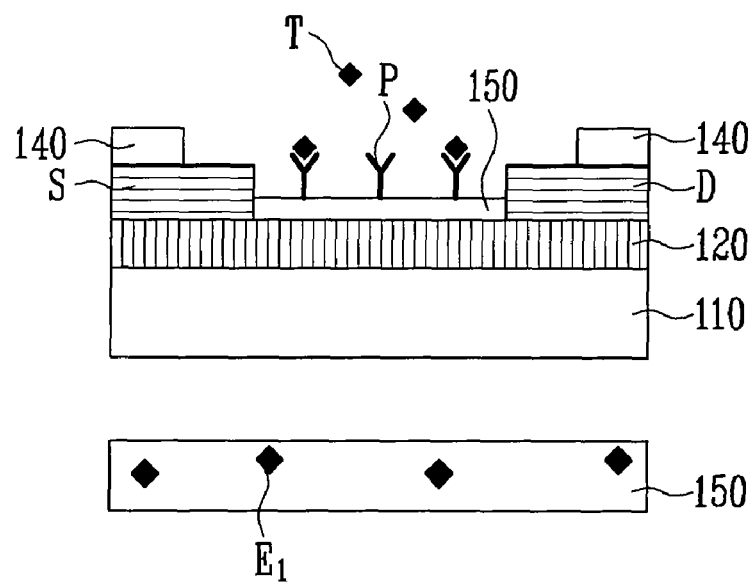
FIGS. 3A to 3C are cross-sectional views showing that conductivity of a silicon nanowire is readily changed by a target molecule to which a nanodot in accordance with the present invention is fixed even though a width of the silicon nanowire is large.
Figure 3B:
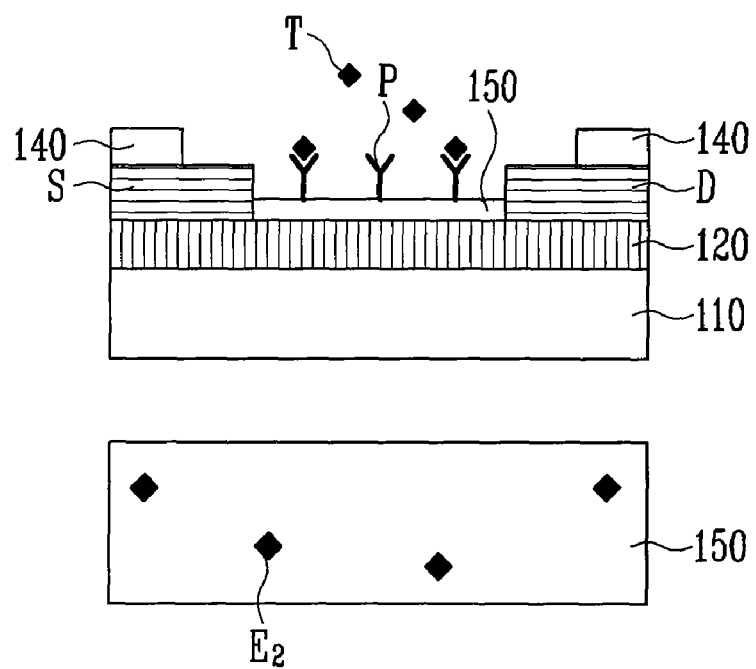
Figure 3C:
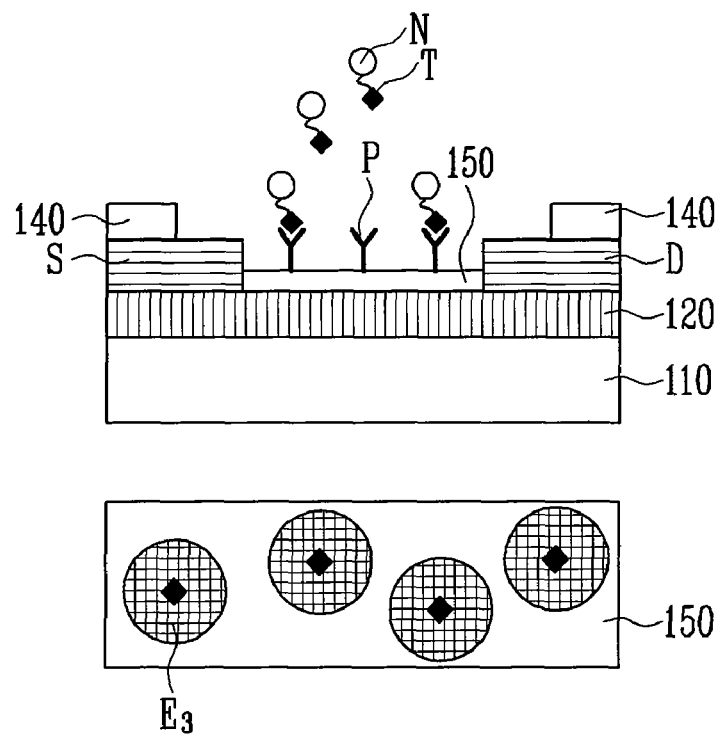
Figure 4:
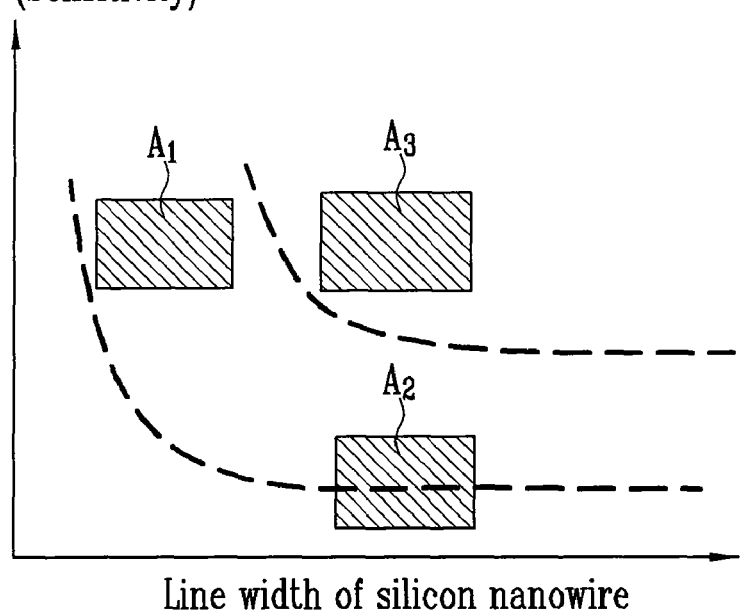
FIG. 4 is a graph showing conductivity (sensitivity) of a silicon nanowire depending on a line width of the silicon nanowire shown in FIGS. 3A to 3C.

FIGS. 3A to 3C are cross-sectional views showing that conductivity of a silicon nanowire is readily changed by a target molecule to which a nanodot in accordance with the present invention is fixed even though a width of the silicon nanowire is large, and FIG. 4 is a graph showing conductivity (sensitivity) of a silicon nanowire depending on a line width of the silicon nanowire shown in FIGS. 3A to 3C.

First, as shown in FIG. 3A, when the line width of the silicon nanowire 150 is small, an electric field region E1 is generated at a surface of the silicon nanowire 150 through a reaction between the target molecules T and the probe molecules P. Since the electric field region $E_1$ has an area relatively larger than that of the silicon nanowire 150, conductivity of the silicon nanowire 150 can be substantially varied as shown in $A_1$ of FIG. 4.

In contrast, as shown in FIG. 3B, when the line width of the silicon nanowire 150 is large, since the electric field region $E_2$ has an area relatively smaller than that of the silicon nanowire 150, conductivity of the silicon nanowire 150 cannot be readily varied as shown in $A_2$ of FIG. 4.

That is, conductivity of the silicon nanowire 150 can be varied by the target molecules T under the condition that the line width of the silicon nanowire 150 is substantially small. However, it is difficult to reduce the line width of the silicon nanowire 150 using the conventional art as described above, thereby making it difficult to increase sensitivity of the biosensor.

For this purpose, the electrically charged nanodots N are coupled to the target molecules T such that conductivity of the silicon nanowire 150 having a large line width can be readily varied. That is, when the electrically charged nanodots N charged are coupled to the target molecules T, even though the line width of the silicon nanowire 150 is large as shown in FIG. 3C, a large electric field region $E_3$ is formed at a surface of the silicon nanowire 150 by the target molecules T to which the nanodots N are coupled, and therefore, conductivity of the silicon nanowire 150 can be substantially varied as shown in $A_3$ of FIG. 4.

Hereinafter, a method of manufacturing a biosensor in accordance with an exemplary embodiment of the present invention will be described with reference to the accompanying drawings.

Figure 5:
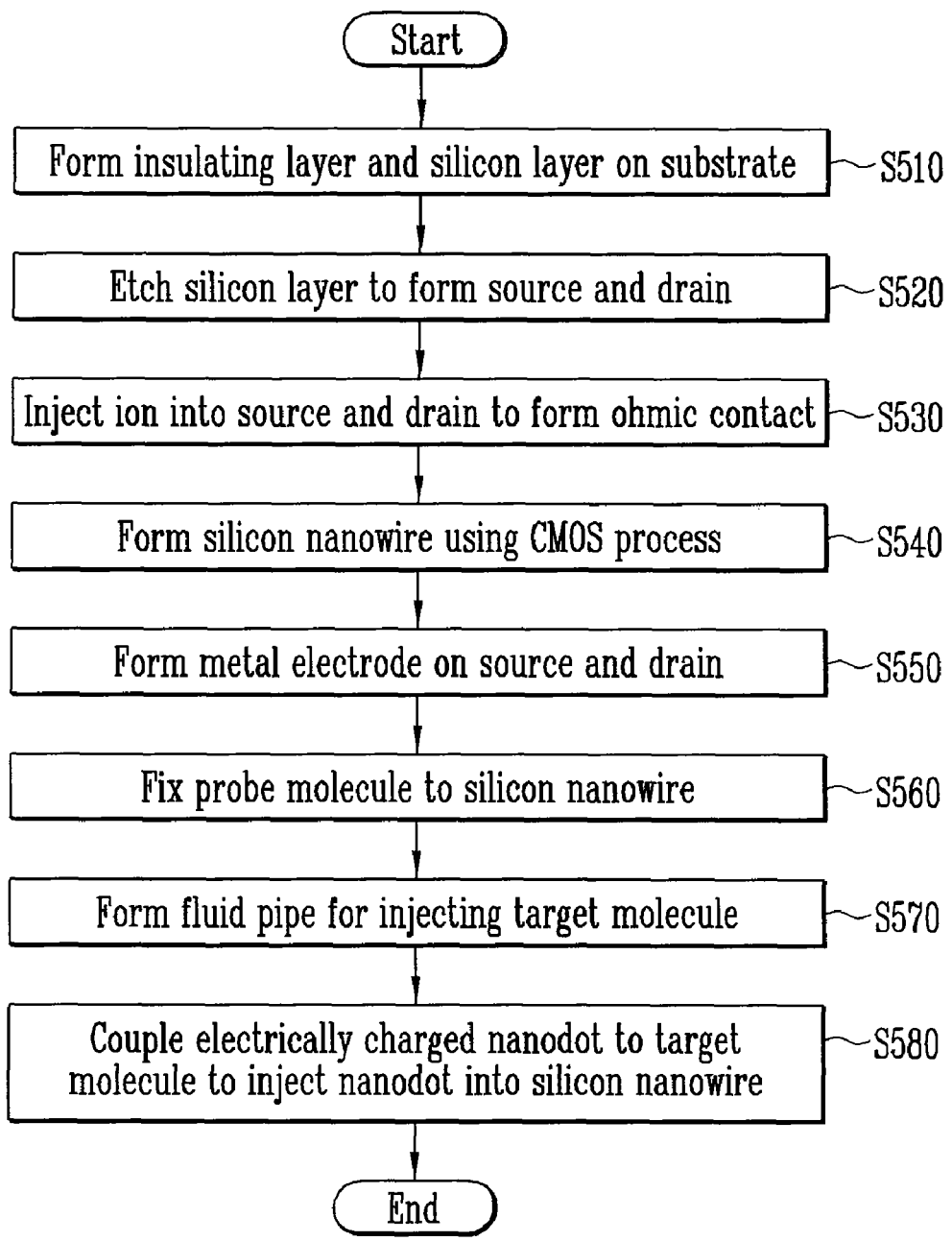
FIG. 5 is a flowchart illustrating a method of manufacturing a biosensor in accordance with an exemplary embodiment of the present invention.

FIG. 5 is a flowchart illustrating a method of manufacturing a biosensor in accordance with an exemplary embodiment of the present invention, and FIGS. 6A to 6F are cross-sectional views of the method of manufacturing a biosensor in accordance with an exemplary embodiment of the present invention.

Figure 6A:
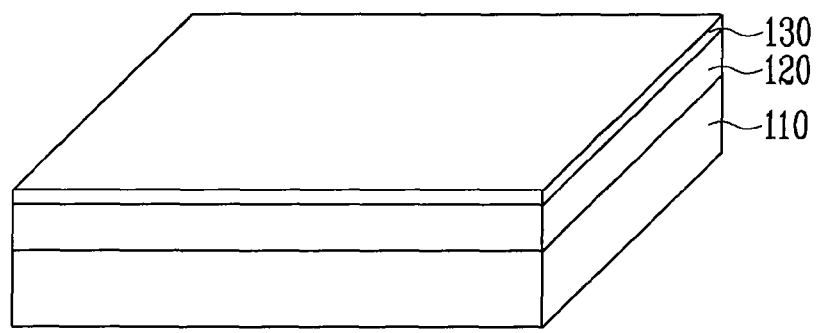
FIGS. 6A to 6F are cross-sectional views illustrating the method of manufacturing a biosensor in accordance with an exemplary embodiment of the present invention.

First, as shown in FIG. 6A, an insulating layer 120 and a silicon layer 130 are formed sequentially on a substrate 110 (S510). Here, the substrate 110 mainly uses a silicon substrate, and the insulating layer 120 may be formed of an oxide layer or a nitride layer. In addition, the silicon layer 130 may be formed of a low concentration silicon layer.

Figure 6B:
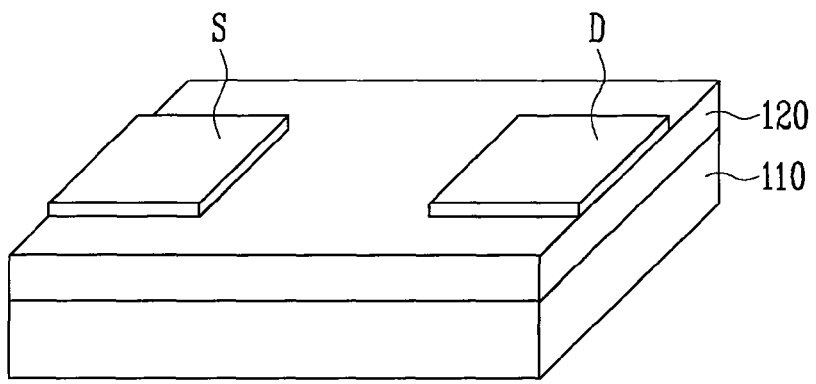

Next, as shown in FIG. 6B, the silicon layer 130 is etched through a photolithography process to form a source S and a drain D (S520).

Figure 6C:
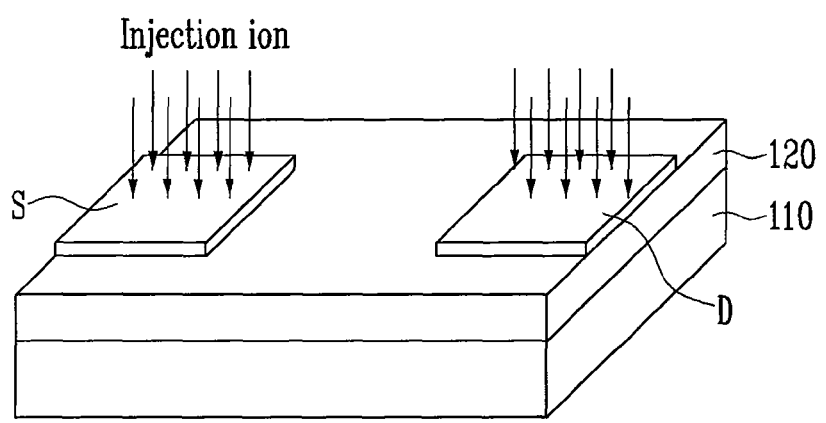

Next, as shown in FIG. 6C, ions are injected into the source S and the drain D to form an ohmic contact (S530).

Figure 6D:
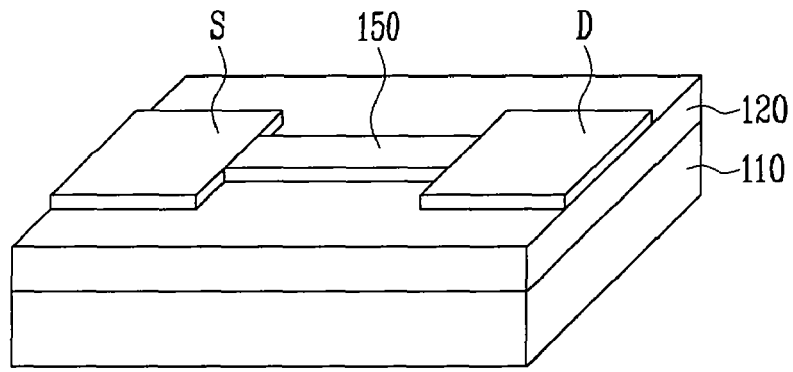

Next, as shown in FIG. 6D, a silicon nanowire 150 is formed between the source S and the drain D by a CMOS process (electron beam lithography) (S540).

Here, a line width of the silicon nanowire 150 may be 10 to 1000 nm, and may be varied depending on a constituent and a size of the nanodot N coupled to the target molecule T.

Figure 6E:
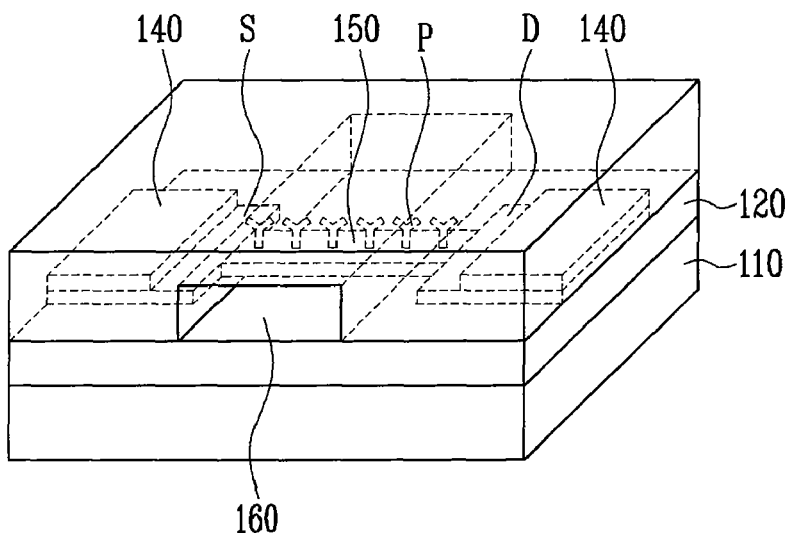

Next, as shown in FIG. 6E, after forming metal electrodes 140 on the source S and the drain D (S550), probe molecules P are fixed to the silicon nanowire 150 (S560). Then, a fluid pipe 160 for injecting target molecules T is formed (S570).

Figure 6F:
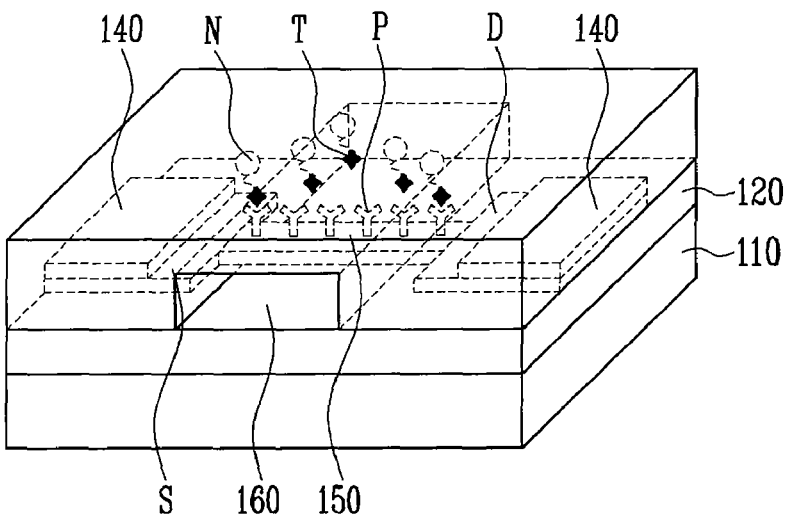

Finally, as shown in FIG. 6F, the electrically charged nanodots N are coupled to the target molecules T to be injected through the fluid pipe 160 (S580).

Here, the electrically charged nanodots N may be formed of a material capable of readily coupling to the target molecules T and being electrically charged, for example, silicon, silicon compound, metal compound, and so on. In addition, the size of the electrically charged nanodots N may be about 1 to 50 nm, and a method of electrically charging nanodots may be an electrical method, in addition to an optical method.

Therefore, while the line width of the silicon nanowire 150 is increased through a CMOS process of the step S540, a large electric field region can be formed at a surface of the silicon nanowire 150 by the target molecules T to which the nanodots N are coupled, and therefore, it is possible to manufacture the biosensor having improved sensitivity.

As can be seen from the foregoing, a silicon nanowire can be formed by a CMOS process to reduce manufacturing cost. In addition, an electrically charged nanodot is coupled to a target molecule to be detected, in order to readily change conductivity of the silicon nanowire, thereby making it possible to implement a biosensor having good sensitivity and being manufactured at a low cost. As a result, the biosensor can be commercialized.

Although the present invention has been described with reference to certain exemplary embodiments thereof, it will be understood by those skilled in the art that a variety of modifications and variations may be made to the present invention without departing from the spirit or scope of the present invention defined in the appended claims, and their equivalents.

What is claimed is:

1. A biosensor using a nanodot, comprising:
    a source and a drain formed on a substrate;
    a silicon nanowire formed between the source and the drain;
    a probe molecule fixed to the silicon nanowire; and
    a fluid pipe configured to receive a target molecule coupled to an electrically charged nanodot,
    wherein the target molecule coupled to the electrically charged nanodot is configured to react with the probe molecule and change electric conductivity of the silicon nanowire.

2. The biosensor according to claim 1, wherein the nanodot is formed of a material capable of readily coupling to the target molecule and being electrically charged.

3. The biosensor according to claim 1, wherein the nanodot has a size of 1 to 50 nm.

4. The biosensor according to claim 1, wherein the silicon nanowire has a line width of 10 to 1000 nm.

5. The biosensor according to claim 1, wherein a line width of the silicon nanowire is determined depending on the type and size of the nanodot.

6. The biosensor according to claim 1, wherein an electric field region of the silicon nanowire is enlarged by the nanodot coupled to the target molecule.

7. A method for sensing biomolecule using a nanodot, comprising:
    preparing a biosensor to detect a target molecule,
        wherein the biosensor comprises:
        a source and a drain formed on a substrate;
        a silicon nanowire formed between the source and the drain;
        a probe molecule fixed to the silicon nanowire; and
        a fluid pipe to receive a target molecule coupled to an electrically charged nanodot;
    coupling the electrically charged nanodot to the target molecule,
    injecting the target molecule coupled to the electrically charged nanodot through the fluid pipe, wherein the target molecule coupled to the electrically charged nanodot is configured to react with the probe molecule and change electric conductivity of the silicon nanowire, and
    detecting the target molecule by measuring the electric conductivity of the silicon nanowire.

\* \* \* \* \*